US008507028B2

(12) United States Patent
Knaggs

(10) Patent No.: US 8,507,028 B2
(45) Date of Patent: Aug. 13, 2013

(54) VISUALIZATION AND ENHANCEMENT OF LATENT FINGERPRINTS USING LOW PRESSURE DYE VAPOR DEPOSITION

(75) Inventor: Calvin Thomas Knaggs, Brampton (CA)

(73) Assignee: Linde North America, Inc., Murray Hill, NJ (US)

( * ) Notice: Subject to any disclaimer, the term of this patent is extended or adjusted under 35 U.S.C. 154(b) by 734 days.

(21) Appl. No.: 12/327,836

(22) Filed: Dec. 4, 2008

(65) Prior Publication Data

US 2010/0143575 A1 Jun. 10, 2010

(51) Int. Cl.
*A61B 5/103* (2006.01)
*A61B 5/117* (2006.01)

(52) U.S. Cl.
USPC ........................................................... 427/1

(58) Field of Classification Search
USPC ........................................................... 427/1
See application file for complete search history.

(56) References Cited

U.S. PATENT DOCUMENTS

| 4,297,383 A | 10/1981 | Bourdon |
| 5,465,765 A * | 11/1995 | Martindale ................ 141/65 |
| 6,157,774 A * | 12/2000 | Komino et al. ............. 392/387 |
| 8,272,343 B1 * | 9/2012 | Weaver et al. ............. 118/31.5 |
| 2002/0124537 A1 | 9/2002 | Manna et al. |
| 2008/0020126 A1 * | 1/2008 | Arndt ............................... 427/1 |

OTHER PUBLICATIONS

"Summer Research Symposium Abstract Index" Summer Research Symposium, Jul. 21, 2007, pp. 6-33.*
L. Tomasevich, M. Leonard, An Intermolecular Conjugate Addition Approach to the Synthesis of Lunamarine, 2007 Summer Research Symposium, 2007, pp. 6-33, Wash-Jeff College, USA.

* cited by examiner

*Primary Examiner* — Kelly M Gambetta
(74) *Attorney, Agent, or Firm* — David A. Hey

(57) ABSTRACT

Methods and apparatus for the recovery, visualization and enhancement of latent fingerprints using Low Pressure Dye Vapor Deposition (LPDVD) are described. The LPDVD methods of the present invention provide for fine control over the deposition of a precursor in combination with a fluorescent dye, combination of dyes or a premixed dry solid compound of the precursor and dyestuffs, to make the latent fingerprints visible. The LPDVD process makes use of a heated carrier gas to dilute and carry the vapors into a vacuum chamber where they condense onto the exposed surfaces of the article being developed. The LPDVD process can be used to develop latent fingerprints on a wide variety of substrates, including metal, plastic, glass and thermal paper and has been shown to perform as well or better than conventional fingerprint development techniques on these surfaces.

11 Claims, 10 Drawing Sheets

VISUALIZATION AND ENHANCEMENT OF LATENT FINGERPRINTS USING LOW PRESSURE DYE VAPOR DEPOSITION

FIELD OF THE INVENTION

The present invention relates to new methods and apparatus for the recovery, visualization and enhancement of latent fingerprints.

BACKGROUND OF THE INVENTION

There are many techniques for developing latent fingerprints on various substrates know in the world of forensic science. Fingerprints consist of approximately 98% water with the remaining 2% being a combination of grease, oil, salts and amino acids. The ability to develop these fingerprints varies with the type of substrate on which they are deposited. Porous substrates such as thermal paper require chemical treatments to develop latent prints, the most commonly used chemical techniques including ninhydrin(triketohydrindene hydrate) spraying, 1,8-diazafluoren-9-one (DFO) treatment, and silver nitrate and iodine fuming. Development of latent prints with ninhydrin depends on a chemical reaction with the amino acids left by the fingerprint to form a purple-blue colored product, Ruhelmann's Purple. The ninhydrin spray is prepared using ninhydrin powder and a suitable solvent, such as acetone or ethanol, or from ninhydrin crystals and a solvent. The use of DFO follows a similar reaction path, wherein amino acids react with the DFO to form a product that fluoresces yellow under green excitation light. There are several disadvantages associated with these conventional methods. In particular, the development of latent prints on thermal paper can take as long as three weeks using conventional ninhydrin methods. Further, the thermal paper can be discolored if the chemicals are not prepared or applied properly, which can result in damage or loss of valuable evidence.

Cyanoacrylate (CA) esters have been used since the late 1970s as an effective means of developing latent fingerprints on non-porous substrates such as glass, plastics and aluminum foil. CA fuming utilizes the CA esters to develop the latent prints by heating liquid CA (e.g. super glue methylcyanoacrylate or ethylcyanoacrylate) so that it reacts with traces of amino acids, fatty acids and proteins in the latent fingerprint and moisture in the air to produce a visible, sticky white material that forms along the ridges of the fingerprint. The final result is an image of the entire latent fingerprint that may be photographed directly but often requires a separate process for further enhancement. Such further enhancement usually comprises treating the article with a premixed liquid dye solution, applied by dipping, spraying, or brushing followed by drying. The disadvantages of using further enhancement processes includes the fact that enhancement dyes are usually mixed by the facility trying to develop the latent prints, which can easily result in inconsistency or errors in formulation and concentration. This can in turn lead to damage or loss of the evidence. In addition, the dye solutions contain solvents that may dissolve the fingerprint residue that has not reacted with the CA. Furthermore, the action of dipping, spraying or brushing the evidence with the dye solution may wash away or wipe away critical evidence.

While the CA procedure represents the most common method for the development of latent fingerprints, it is relatively complex and time consuming. In particular, to enable the reaction to take place, the CA must be in gaseous form, which is generally accomplished by placing the article into a fuming chamber or an airtight tank having a small heater. A few drops of liquid CA are then placed into a tiny, open container and the container is placed on top of the heater inside the tank. The tank is then carefully sealed but remains at atmospheric pressure and the heater is activated. The boiling point for most CAs varies between 49° C. and 65° C. (120° F. and 150° F.) depending on the chemical composition. When the CA in the container reaches the boiling point it will boil away into the surrounding atmosphere to create a concentration of gaseous CA. If any latent fingerprints exist anywhere inside the tank, they will eventually be exposed to the gaseous CA and the natural humidity contained in the atmosphere is enough to trigger the reaction. The whole reaction can take over two hours depending on the size of the tank, the concentration of the gaseous CA in the air, the humidity in the air and numerous other factors. There are a number of disadvantages associated with using CA development processes, including overdevelopment when polymerization occurs between the fingerprint ridges and excess development beyond the ridges that make it difficult to distinguish the print from the background. In addition, CA polymerizes to form a white material that may not provide contrast against a white background, again making distinguishing of the print difficult. This often results in the need for further enhancement, e.g. the use of fluorescent dyes to visualize the prints.

Another method for developing latent fingerprints is through the use of Physical Vapor Deposition (PVD), the most common method being Vacuum Metal Deposition (VMD). When a human fingerprint touches a surface, a sweat deposit, i.e. the fingerprint is left behind on the surface. A standard VMD method uses a vacuum chamber and thermal sources to evaporate two thin layers, one of gold and the other of zinc, onto the suspect material. The material is loaded into a vacuum chamber and the pressure is lowered to approximately 1 millionth of an atmosphere ($10^{-4}$ mbar). Gold is then evaporated, deposits uniformly over the surface and is absorbed by the ridges of the human sweat that form the invisible fingerprint pattern. Zinc is then evaporated and because zinc generally condenses only onto another metal, it adheres only to the gold coated areas that lie between the sweat ridges to create a visible pattern defining the latent fingerprint image. This method of developing fingerprints is again relatively complex and time consuming, as well as costly.

There is a need in the art for improvements in the development and enhancement of latent fingerprints.

SUMMARY OF THE INVENTION

The present invention provides new methods and apparatus for the recovery, visualization and enhancement of latent fingerprints using Low Pressure Dye Vapor Deposition (LPDVD). The LPDVD methods of the present invention provide a controlled deposition of a precursor followed by a fluorescent dye, combination of dyes or co-deposition of the precursor and dye stuffs premixed as a dry solid compound to make the latent fingerprints visible.

DETAILED DESCRIPTION OF PREFERRED EMBODIMENTS

The present invention provides new methods and apparatus for the recovery, visualization and enhancement of latent fingerprints using Low Pressure Dye Vapor Deposition (LPDVD). The LPDVD methods of the present invention provide a controlled deposition of a precursor followed by a fluorescent dye, combination of dyes or co-deposition of the precursor and dye stuffs premixed as a dry solid compound to make the latent fingerprints visible.

The LPDVD method of the present invention can be used on a wide variety of substrates, including non-porous metal, glass and plastic as well as porous thermal paper. As noted, the basic methodology of the LPDVD methods of the present invention involves the use of a precursor in combination with a controlled deposition of a fluorescent dye, combination of dyes or co-deposition of a premixed dry solid compound, wherein the dye stuffs are either sublimated or evaporated in a low pressure environment and condense onto the exposed surfaces of the substrate. Use of the LPDVD methods of the present invention allow for noncontact application of fluorescent dye(s) that will adhere to the latent fingerprints and that can be viewed and controlled so that development and visualization can be optimized. The LPDVD methods of the present invention are at least equal to and in some cases more effective then the conventional CA fuming, fluorescent dye enhancement and dry ninhydrin methods.

Figure 10:
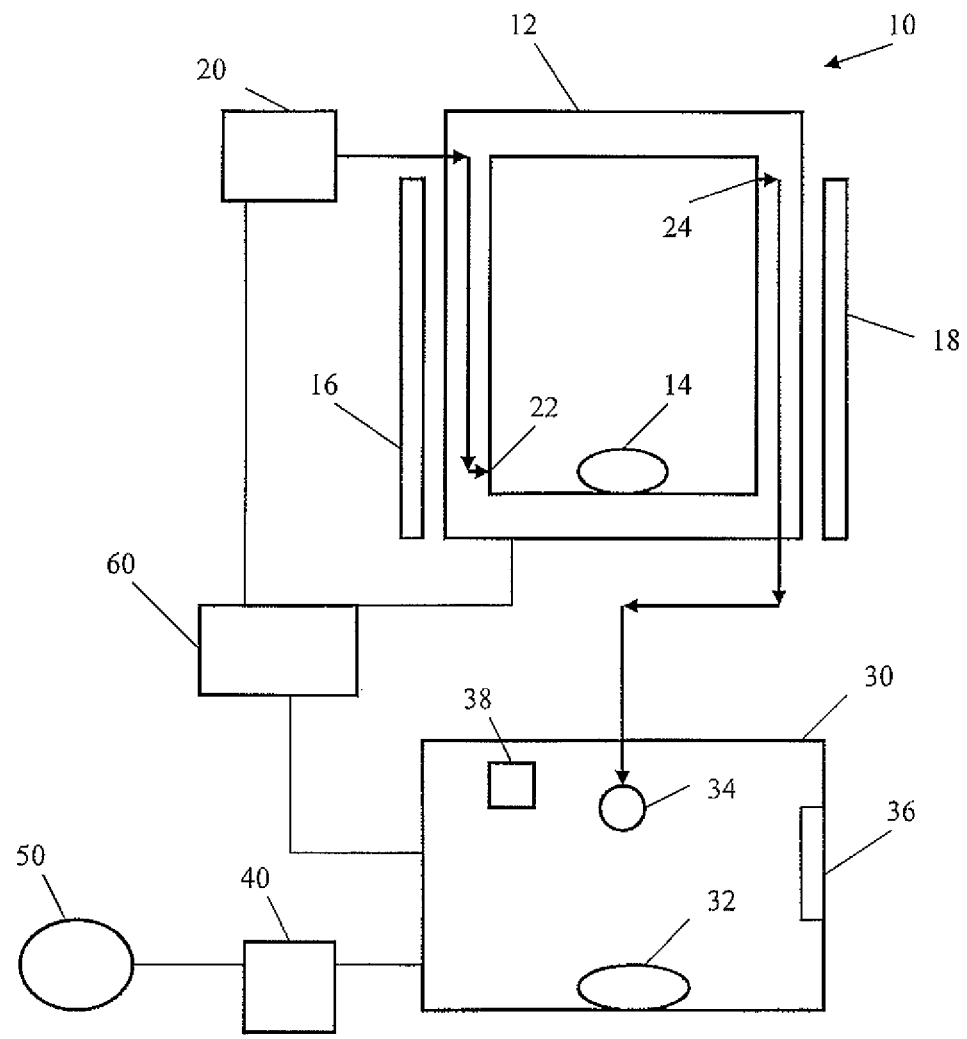
FIG. 10 is a schematic drawing of an apparatus according to one embodiment of the present invention.

The LPDVD processes of the present invention can be carried out using the apparatus shown in FIG. 10. The apparatus comprises a vapor delivery system 10, having a delivery chamber 12, for heating source materials 14, using heaters 16, 18. The vapor delivery system 10, also includes a carrier gas source 20, in connection with an inlet 22, to the delivery chamber 12. An outlet 24, of the delivery chamber 12, is connected to a nozzle 34, located in a vacuum chamber 30, that is used for the LPDVD process to develop latent fingerprints on an article 32. The vacuum chamber 30, also includes a viewing window 3 6, and an excitation light source 38, and is connected to an exhaust filter 40, and system vacuum pump 50. An optional controller 60, is connected to the various components of the system.

The LPDVD process of the present invention will be described below with reference to FIG. 10. Initially, the articles 32, of evidence are placed or suspended inside the vacuum chamber 30. The delivery chamber 12, of the vapor delivery system 10, is loaded with source materials 14, comprising polycyanoacrylate and a chosen dye or premixed dry solid compound consisting of polycyanoacrylate and a dye material. The delivery chamber 12, is then sealed and pumped down to a predetermined pressure using the vacuum pump 50. Pressure measurement and set points are monitored and controlled manually using the readings from vacuum gauges or alternatively using the controller 60, such as a PC or PLC control system. The excitation light source 38, is turned on, focused on the article 32, and set to optimum excitation wavelength for the dye being used. The vapor delivery system 10, is turned on and allowed to ramp up to a preset temperature using the heaters 16, 18, causing the source material 14, to either sublimate or evaporate. As the temperature of the vapor delivery system rises, a metered flow of carrier gas, preferably nitrogen gas, from the carrier gas source 20, enters the delivery chamber 12, through the inlet 22, and is heated to the same temperature as the source material 14. As the source material 14, undergoes phase change from solid to vapor, they are diluted by the carrier gas and carried into the vacuum chamber 30, via the nozzle 34. Upon entering the vacuum chamber 30, the gases (vapors) rapidly expand in all directions and condense onto the exposed surfaces of the article 32, (the evidence). The source materials are preferentially deposited on to the ridges of the fingerprints or the background creating contrast to make what were invisible prints become visible. The deposition rate and thickness of the source material can be controlled by adjusting the temperature of the vapor delivery system 10, regulating the mass flow of the carrier gas and by changing the duration of the deposition. The development can be viewed through the viewing window 36, using the unaided eye or with the aid of an excitation light source 38, which causes the deposited dyes to fluoresce. The process can be terminated, continued or repeated until optimum visualization has been achieved. To terminate the deposition, the operator turns off the vapor delivery system 10, which cools rapidly causing the source material 14, to once again undergo a phase change, this time from gas to solid. This effectively terminates the deposition process. The flow of carrier gas is then shut off, the vacuum chamber 30, is isolated from the vacuum pump 60, and vented to atmosphere so that the articles 32, (evidence) can be retrieved for further assessment or photography. The exhaust filter 40, such as a chemical trap, can be used to remove pollutant materials from the exhaust stream for further treatment or abatement.

The LPDVD methods can be used to deposit polycyanoacrylate alone or in combination with dyestuffs for farther enhancement. Alternatively, the polycyanoacrylate and the dyes for the LPDVD methods of the present invention can be premixed as a dry solid compound and co-deposited. In addition, the dyes can be chosen from a wide variety of known and available dyes, including fluorescent, non-fluorescent or near infrared dyes. Fluorescent dyes that can be used include rhodamine 6G, D2 yellow, ardrox, brilliant yellow, Photosecure UY1, and others. Example of non-fluorescent dyes include those from the anthraquinone family commonly used in thermal dry printers for example. One example of a near infrared dye is Photosecure N84, having peak emission in the 830 nm range, that can be visualized or photographed using an infrared camera.

The LPDVD methods of the present invention provide a number of advantages, particularly with respect to the conventional methods noted above. For example, LPDVD methods use polycyanoacrylate and a dye or combination or dyes to develop the latent print, but do not use metals as required when using VMD methods. Further, the LPDVD methods can operate within a much broader pressure range, i.e. $10^{-2}$ mbar compared to the pressure range required for VMD methods (i.e. $10^{-4}$ mbar or less). In addition, the LPDVD methods use solid forms of polycyanoacrylate and dyes that can be premixed as a dry solid compound which allows for greater batch to batch control, consistency and repeatability of formulation. As noted above the known methods often require a separate enhancement step to provide useful visualization of prints, but which also add significant risks of damage or loss of the evidence. Enhancement of the prints using LPDVD methods is a one step process completed in one process run thus saving time and avoiding additional steps that may damage the evidence through physical contact with the substrate; e.g. spraying, brushing, dipping or drying.

The use of solid premixed source materials provides much greater consistency when using LPDVD methods. In particular, use of these dry compounds avoids the problems associated with mixtures of liquids noted above with respect to the prior art methods. Further, there is no need to dip, brush, spray or dry substrates as required in conventional methods and therefore LPDVD methods do not allow substrates to contact liquids that might be absorbed or discolor the surface and possibly destroy the print. Because the LPDVD methods use solid materials, they are also safer, because there is no need to premix chemicals that can create fumes or vapors. In addition, because processing takes place under vacuum any effluent from the process can be purged from the system and vented through a filter (e.g. a carbon filter), there is virtually no risk of leakage of fumes or vapors, as might occur in the CA fuming and or enhancement techniques of the prior art.

The LPDVD methods of the present invention provide a single method that can be used for development of prints on a wide range of substrates, both porous and non-porous. This replaces as many as three separate and different conventional processes currently in use. LPDVD techniques can develop prints on thermal paper in as little as 30 to 60 minutes with no further enhancement needed. This is significantly less than the three weeks sometimes needed when using conventional methods.

The LPDVD methods of the present invention allow for optimization and precision control of the deposition process and therefore nearly eliminates the possibility of over fuming and overdevelopment that can occur when fuming CA or applying excess liquid dyes as required in the prior art. Deposition of polycyanoacrylate and dyes does not begin until the system is pumped down to the desired pressure. The results from using the LPDVD methods are much more consistent because of the greater control possibilities. The operator can precisely control rate, uniformity and film thickness for optimal visualization of the latent print. Dyes can be deposited with very uniform thicknesses across the entire substrate, thereby avoiding blotching, and missed spots as well as under or over developed areas that often occur when using liquid based dyes in the prior art methods. The concentration and film thickness of the dye affects the fluorescent response when exposed to excitation light. If the concentration of the dyes is too low or too high, there will be less than optimum fluorescence. If the deposited film thickness is too low or too high, there will be less than an optimum response. The LPDVD methods provide for superior control over both the dye concentration and the film thickness, therefore making it much easier to achieve the highest fluorescent response. There is far greater control of concentration and deposited film thickness than when using conventional liquid based dyes applied by spraying, dipping, brushing and finally drying. This lack of control can result in dye concentrations being inaccurate and inconsistent, especially during the mixing process and film thickness of the dye when dried is extremely variable. Therefore, the LPDVD methods of the present invention provide superior control and film thickness utilization of the dye leading to optimum fluorescence response. In addition, the LPDVD methods of the present invention are very flexible, allowing the operator to develop, take photographs and reprocess the article to try to develop more detail if necessary.

The LPDVD methods of the present invention allow for minimum heat contacting the surface of the article. Although the carrier gas is heated to relatively high temperatures, up to 600° C. in the vapor delivery system, the low mass flow and rapid expansion upon entering the vacuum chamber results in no significant heat buildup on the exposed surfaces during the deposition process. The process therefore operates essentially at room temperature unless there is a desire to artificially heat the substrate prior to or during the process.

The following tests and experimental data show the superior results that can be achieved when using the LPDVD methods of the present invention.

Sample fingerprints were collected from a number of different male and female volunteers. Before print deposition, each volunteer followed a stringent hand washing protocol: i.e. 1) wash hands thoroughly with soap and warm water, 2) dry hands using a non-contact air dryer, and 3) wipe hands with an alcohol swab. Once their hands were clean, each volunteer placed non-powdered nitrile gloves over their hands to promote sweating and prevent the hands from collecting contaminants. After a 15-minute period, each volunteer removed the gloves and touched their nose and forehead prior to depositing a series of depleted prints on the designated substrate. Thus the deposits consisted of both eccrine and sebaceous secretions. Only one finger was utilized at a time and each finger was used to deposit 10 fingerprints subsequently. The volunteers did not touch anything between each fingerprint deposition. While the hand washing regiment and protection of the deposited fingerprints represents an ideal situation that would rarely be found in the real world, it did accommodate the main purpose of this study, i.e. to determine the general efficacy of the LPDVD process.

Figure 1:
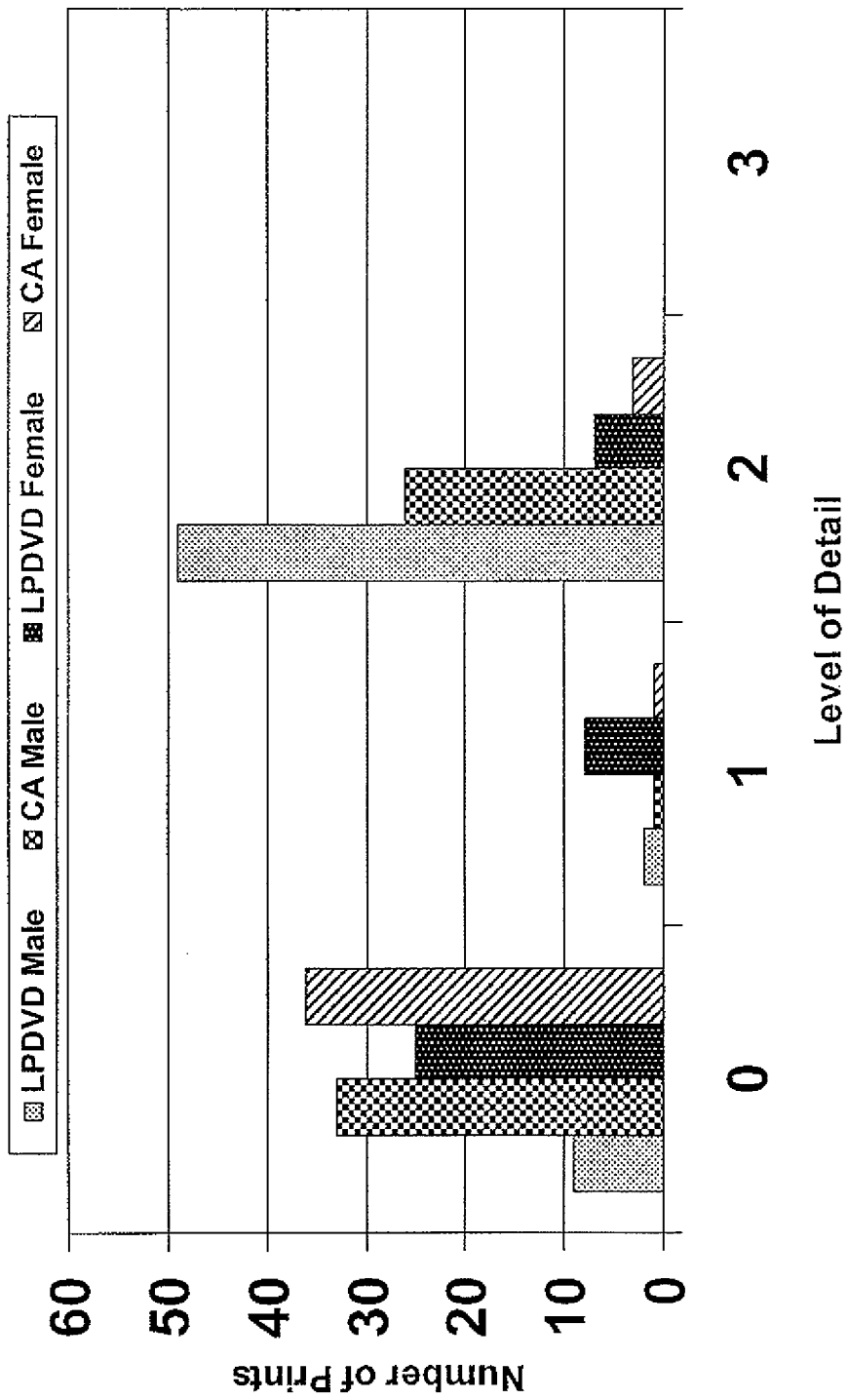
FIG. 1 is a graph showing results of tests performed on aluminum substrates 24 hours after fingerprint deposition.

Several different substrates were chosen: 1) Glad® Kitchen catcher white, anti-odor plastic bags (made by Clorox®, 60.9×71 cm), 2) microscope slide (Sail Brand, Cat. No. 7101, 25.4×76.2 mm), 3) Alcan® aluminum foil (30.5 cm×76.2 m), and 4) Maxwell® thermal paper (No. 54010—Mfg Appleton—N-30230 4407N036A). The Glad® Kitchen catcher plastic bags were stretched over a piece of cardboard the same size as the bag with a grid placed over the plastic bag. This grid was composed of 10 columns each with 10 oval shaped slots as shown in FIG. 1. The columns were numbered from 1 to 10 and each slot was divided into A and B sides so that each slot area was cut in half before print deposition to avoid destroying the fingerprint once it had been deposited. The separation of the slot areas allowed the deposited fingerprint to be easily separated into two portions. Fingerprints were deposited on the exterior of the bag and each column was labeled with the sampling date, substrate description, and spaces to enter the processing date and gender of the donor (M for male and F for female). Each print was assigned a number from 1-10 and a letter A for the left-half or B for the right-half. Once the prints were deposited and the information recorded, the grid was removed and the prints were separated. The halves were than randomly distributed between processing by the LPDVD process and by a conventional CA fuming process. For the plastic bag substrates, a total of 100 prints were developed by each process in 24-hour and 60-day assessments. After processing, the bags were kept in cardboard boxes to prevent dust collection before assessment.

The above procedure was repeated for the three other substrates; i.e. glass (microscope slides), aluminum foil and thermal paper. For the microscope slides, each column was composed of 5 microscope slides in length and 2 slides in width and each slide had 2 prints deposited thereon. The thermal paper was tested on both the front and back side. However, in the 60 day sample processes, a number of the samples were damaged and removed from the study. Therefore, the 60 day samples (front and back side) were grouped together and not differentiated.

As noted, half of all substrate samples were processed using the LPDVD methods of the present invention as described above. The other half of the plastic, glass and aluminum foil substrates were processed using a conventional CA fuming technique followed by treatment with Rhodamine 6G, while the other half of the thermal paper samples were processed using a conventional ninhydrin method. All of the methods used rhodamine 6G dye as a standard dye throughout the study. Further, all samples were processed on the same day regardless of the method used. Some preliminary tests were carried out to determine how much dye to apply in the LPDVD process as the instrument and process were new and not entirely perfected. This also provided insight on how to use the instrument and process and therefore to ensure consistent processing of the samples.

As noted, the plastic bags, the microscope slides and the aluminum foil were developed using CA fuming, followed by the application of rhodamine 6G dye stain. The CA fuming was completed using a Misonix CA-3000 fuming chamber that was fully automated and controlled humidity, temperature and time. The humidity was kept at 80%, and samples were run through 2 cycles, a 15-minute fuming cycle where the superglue is vaporized in the chamber, and a 20-minute purge cycle that completely evacuates any residual cyanoacrylate fumes. The rhodamine 6G dye was applied using a spray bottle under a fume hood.

The thermal paper was processed with dry ninhydrin using standard technique. Blotting paper was soaked in the ninhydrin solution and allowed to dry. The thermal paper samples were then placed between two pieces of the treated blotting paper and sealed within a standard Ziploc® bag and allowed to sit for two weeks before being removed for assessment.

The developed fingerprints from all methods were assessed and compared by forensic identification officers. These assessments were carried out using a Polilight (Rofin, Australia) having a wavelength range of 425 nm to 530 nm. An excitation wavelength of 530 nm, orange barrier filter and orange viewing goggles were used to visualize the prints. Each print was examined thoroughly and given a score of 0, 1, 2 or 3 to signify the level of detail present. A score of 0 indicated no ridge detail. A score of 1 indicated Level 1 detail, i.e. basic fingerprint patterns of loops, whorls and arches. A score of 2 indicated Level 2 detail, i.e. major ridge events such as bifurcations, ridge endings, short ridges etc. A score of 3 indicated Level 3 detail, i.e. individual ridge detail such as the shape and width of ridges, incipient ridges, and the relative location of pores. In many prints there was more then one level of detail present, e.g. some prints showed Level 1 and 2 detail in the center of the print and Level 2 or 3 around the periphery. In these cases, the lowest level of detail was taken for statistical purposes to prevent positive skewing of the results on either side. The preferred print was also indicated in cases were possible. The microscope slides had to be placed on an angle when being assessed in order to minimize background distortion resulting from excess dye.

The collected data was recorded and is set forth in the following tables. Table 1 contains the data for each substrate type for the 24 hour processing. In addition, the same data is shown in graphic form in FIGS. 1-5.

TABLE 1

24 Hour Assessment Results

| Substrate | Level of Detail | Male | | Female | |
|---|---|---|---|---|---|
| | | LPDVD n = 60 | CA n = 60 | LPDVD n = 40 | CA n = 40 |
| Aluminum Foil | 0 | 9 | 33 | 25 | 36 |
| | 1 | 2 | 1 | 8 | 1 |
| | 2 | 49 | 26 | 7 | 3 |
| | 3 | 0 | 0 | 0 | 0 |
| Plastic Bag | 0 | 18 | 13 | 37 | 26 |
| | 1 | 12 | 12 | 2 | 5 |
| | 2 | 22 | 25 | 1 | 7 |
| | 3 | 8 | 10 | 0 | 2 |
| Microscope Slide | 0 | 6 | 17 | 35 | 40 |
| | 1 | 7 | 2 | 0 | 0 |
| | 2 | 47 | 41 | 5 | 0 |
| | 3 | 0 | 0 | 0 | 0 |
| | | LPDVD n = 60 | CA n = 60 | LPDVD n = 20 | CA n = 20 |
| Thermal Paper (Front Side) | 0 | 42 | 60 | 10 | 20 |
| | 1 | 0 | 0 | 0 | 0 |
| | 2 | 18 | 0 | 10 | 0 |
| | 3 | 0 | 0 | 0 | 0 |
| | | LPDVD n = 20 | CA n = 20 | LPDVD n = 30 | CA n = 30 |
| Thermal Paper (Back Side) | 0 | 2 | 20 | 30 | 30 |
| | 1 | 2 | 0 | 0 | 0 |
| | 2 | 16 | 0 | 0 | 0 |
| | 3 | 0 | 0 | 0 | 0 |

Table 2 shows the data that was collected for each substrate following 60 days and illustrates the ability of the LPDVD process of the present invention to develop aged latent fingerprints from the four different substrates in comparison to conventional CA and dry ninhydrin methods. This data is also shown in graphic form in FIGS. 6-9.

TABLE 2

60 Day Assessment Results

| Substrate | Level of Detail | Male | | Female | |
|---|---|---|---|---|---|
| | | LPDVD n = 40 | CA n = 40 | LPDVD n = 60 | CA n = 60 |
| Aluminum Foil | 0 | 27 | 18 | 49 | 54 |
| | 1 | 2 | 0 | 3 | 2 |
| | 2 | 11 | 22 | 8 | 4 |
| | 3 | 0 | 0 | 0 | 0 |
| Plastic Bag | 0 | 3 | 1 | 54 | 49 |
| | 1 | 5 | 8 | 0 | 3 |
| | 2 | 32 | 31 | 6 | 8 |
| | 3 | 0 | 0 | 0 | 0 |
| Microscope Slide | 0 | 15 | 22 | 54 | 57 |
| | 1 | 2 | 0 | 3 | 2 |
| | 2 | 23 | 18 | 3 | 1 |
| | 3 | 0 | 0 | 0 | 0 |
| | | LPDVD n = 20 | CA n = 20 | LPDVD n = 30 | CA n = 30 |
| Thermal Paper | 0 | 16 | 20 | 30 | 30 |
| | 1 | 2 | 0 | 0 | 0 |
| | 2 | 2 | 0 | 0 | 0 |
| | 3 | 0 | 0 | 0 | 0 |

The value of the LPDVD process according to the present invention as compared to the conventional CA and dry ninhydrin methods is clearly evident from the collected data. In particular, it is clear that the LPDVD process can be used to develop latent fingerprints on all four types of substrates tested, as opposed to the need for two different conventional processes to accomplish the same coverage of all four substrates.

The results obtained for both male and female prints after 24 hours on aluminum foil are shown in Table 1 and on FIG. 1 and clearly show that the LPDVD process is viable compared to CA fuming. In fact, the LPDVD process was able to develop 23 (38%) more Level 2 detail from the male prints (total n-120) than the conventional CA fuming method. In other words, the LPDVD process was able to develop a total of 49 (81.6%) of the male prints with at least Level 2 detail whereas the conventional CA methods were only able to develop 26 (43.3%) of the male prints at Level 2 detail. The female prints (total n=80) were significantly less effective in showing any differences between the two processes. This is believed to be because of the poor quality of the sample prints. However, the results show that even though the quality of the prints was poor, the LPDVD process was still able to develop 15 of 40 (37.5%) female prints with at Level 1 or Level 2 detail compared to only 4 of 40 (10%) when using the conventional CA. From this test and result, it was shown that the LPDVD of the present invention was superior in developing fingerprints on aluminum foil 24 hours after deposition.

Figure 6:
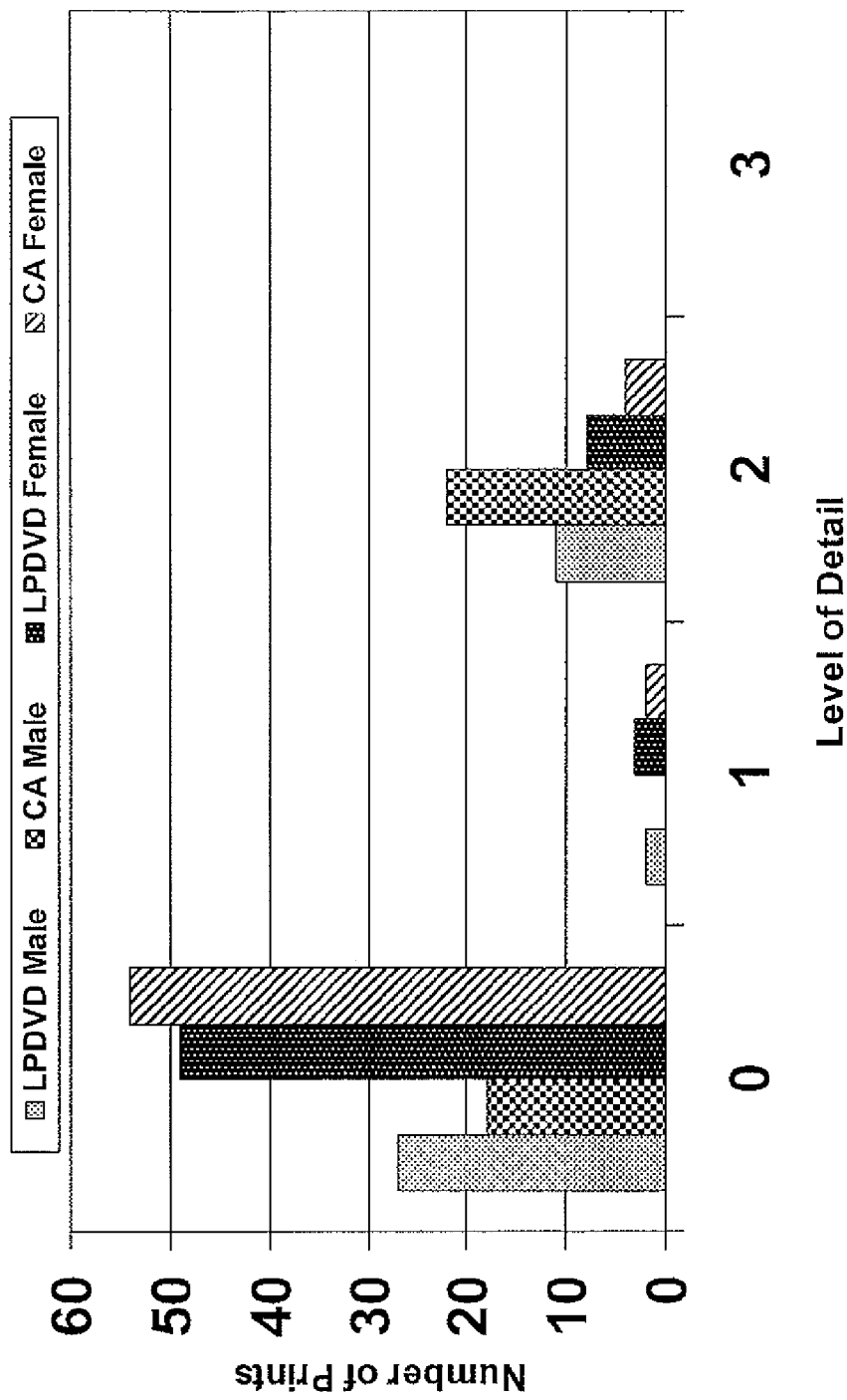
FIG. 6 is a graph showing results of tests performed on aluminum substrates 60 days after fingerprint deposition.

The 60 day old samples on aluminum foil exhibited prints that were not nearly as well developed as the 24 hour samples as shown in Table 2 and FIG. 6. This is a result of the evaporation of the oils and residues left by the finger on the substrate or possibly because of improper deposition of the fingerprints. In any event, the amount of prints showing any level of detail significantly decreased for the 60 day samples as compared to the 24 hour samples. For the 60 day samples on aluminum foil, the LPDVD process was able to detect 13 male prints and 11 female prints with Level 1 and 2 detail which amounts to 24% of the total prints processed using LPDVD. The conventional CA fuming process was able to obtain 28% of the prints (total n=100) at Level 1 and Level 2 detail. The conventional CA method found a total number of 26 Level 2 detail prints compared with 19 Level 2 prints when using the LPDVD process. Therefore, for the 60 day samples, the conventional CA method was slightly better in developing Level 2 identifiable prints.

Figure 2:
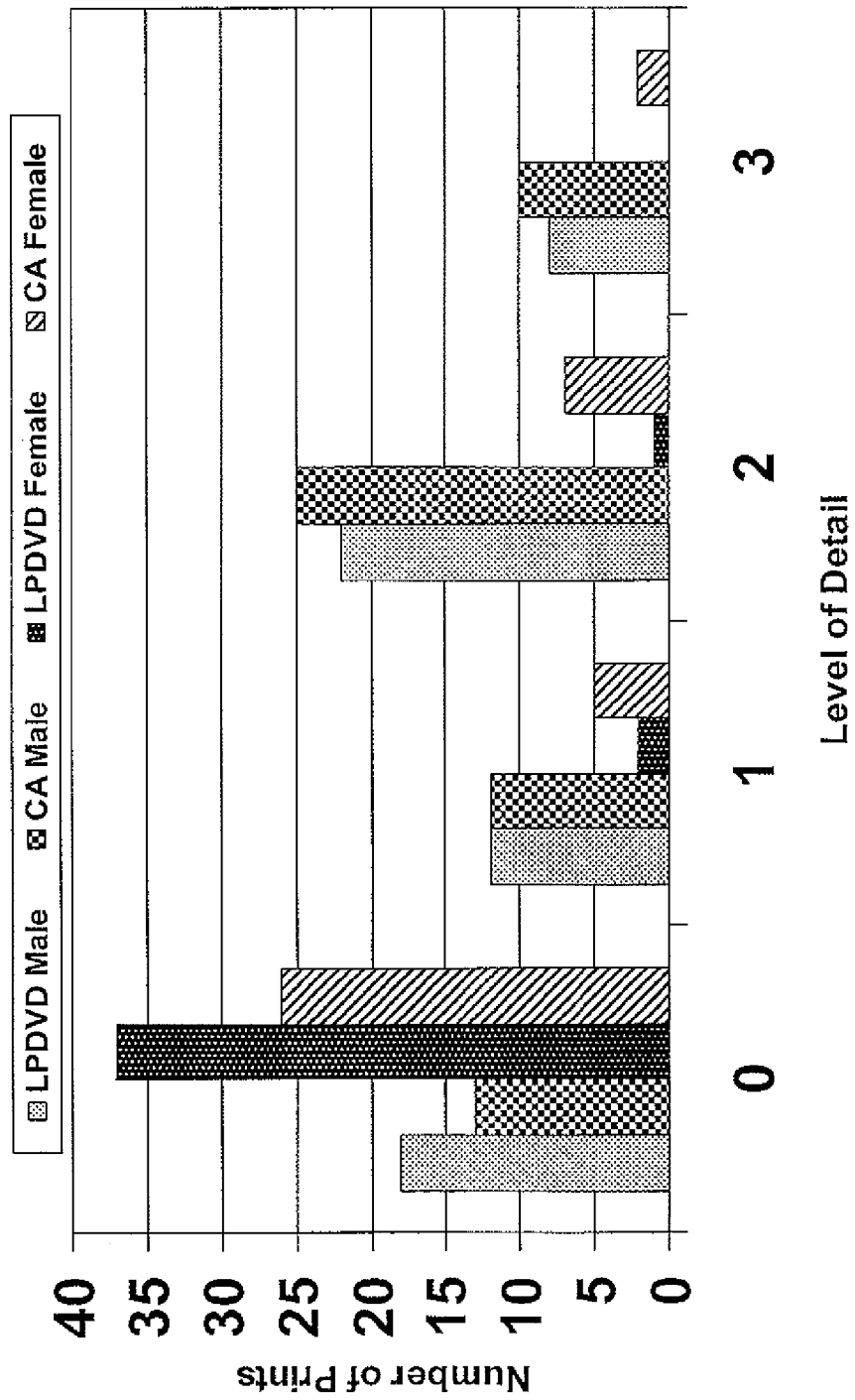
FIG. 2 is a graph showing results of tests performed on plastic bag substrates 24 hours after fingerprint deposition.

The 24 hour samples on plastic bags again show that the LPDVD process is viable as seen from Table 1 and FIG. 2. However, the conventional CA fuming method provided slightly better results for both the male and female prints. It is noted that this was one of the few instances that the female prints produced results of any significance. In particular, the CA fuming process was able to develop 14 (n=40) of the female prints at Level 1, Level 2 and Level 3 detail (35%), whereas the LPDVD process was only able to develop 3 prints (n=40) at Level 1 and Level 2 detail (7.5%). It is possible that this is because of the sensitivity of the LPDVD process but cannot be confirmed as sensitivity was not a tested parameter. The male prints on the other hand yielded similar results for both processes. In 56 instances that the investigator recorded any preference, the CA fuming prints were preferred 44 times (78.5%).

Figure 7:
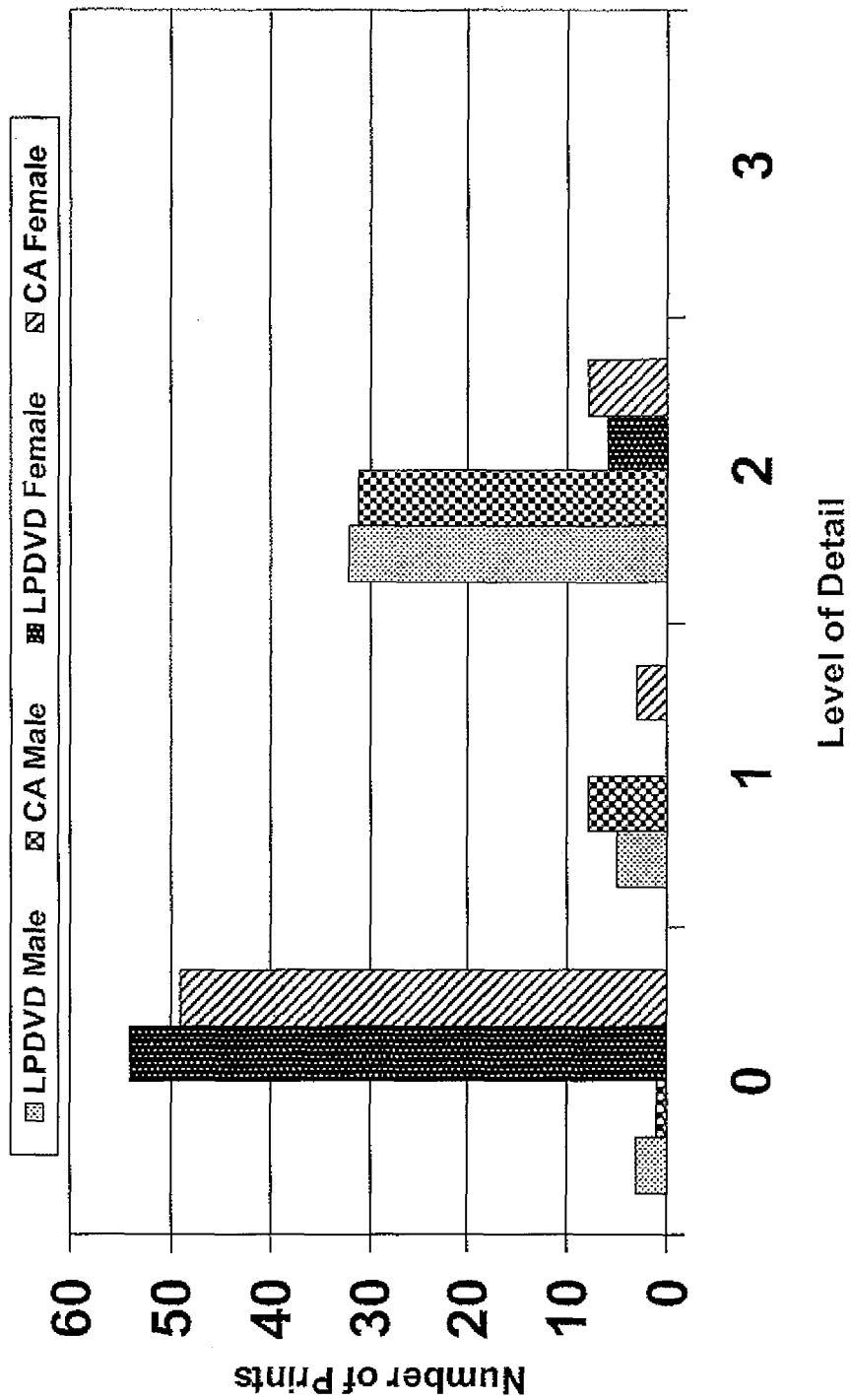
FIG. 7 is a graph showing results of tests performed on plastic bag substrates 60 days after fingerprint deposition.

Table 2 and FIG. 7 show the results for the 60 day old prints on the plastic bag substrates to be very similar to those found from the 24 hour samples. The total of male prints showing Level 2 detail using the LPDVD process was one better than when using the CA process, and the total female prints showing Level 2 detail using the LPDVD process was two fewer than when using the CA process. Again there were a large number of prints having no detail for the female samples, although a larger proportion of male prints were developed after 60 days then were developed after 24 hours. The 24 hour results were more sensitive having a total of 20 prints with Level 3 detail whereas the 60 day samples had no Level 3 detail present. Preferences were recorded for 34 of the 40 male prints with CA fuming being preferred 26 times.

Figure 3:
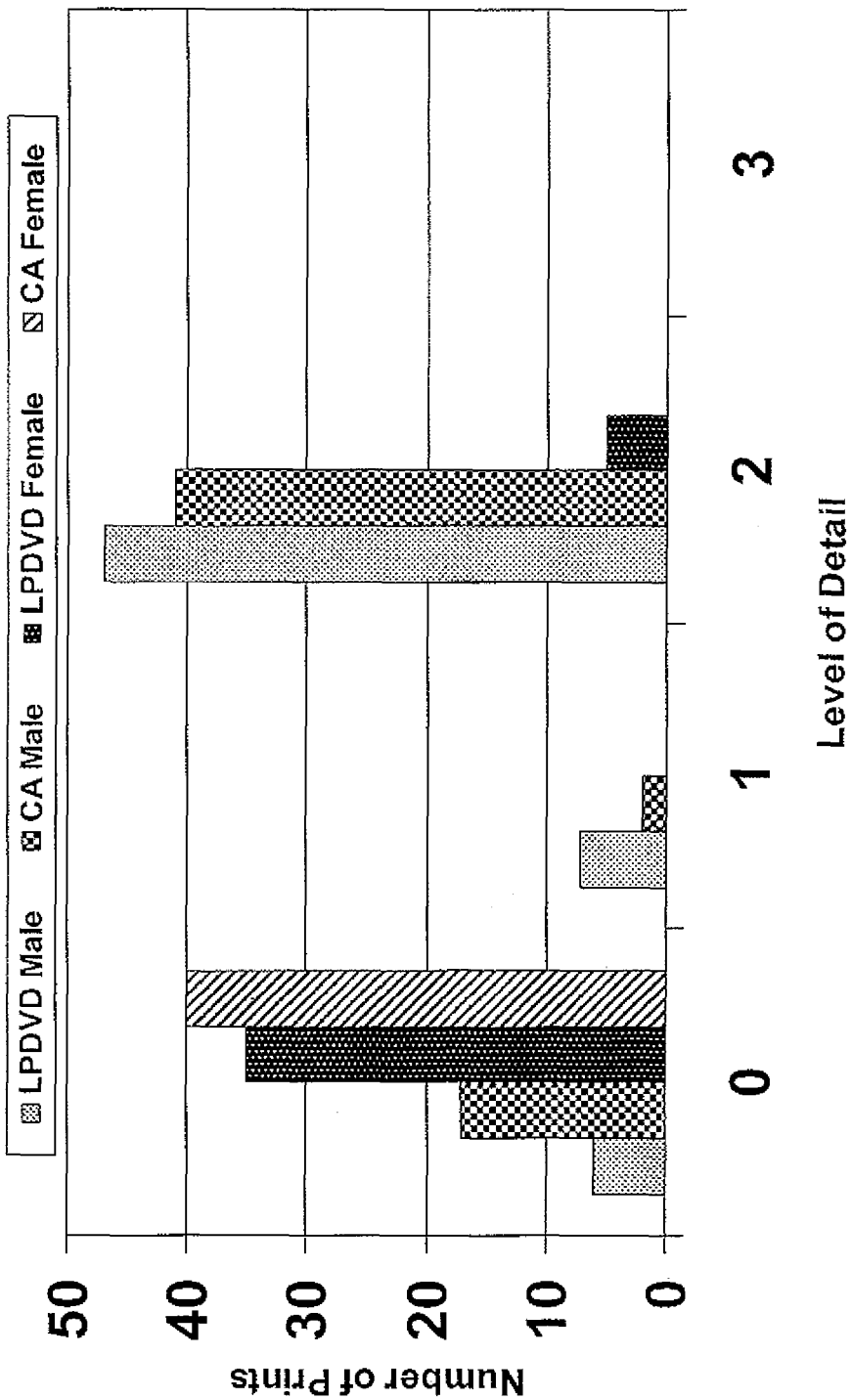
FIG. 3 is a graph showing results of tests performed on glass 24 hours after fingerprint deposition.
Figure 4:
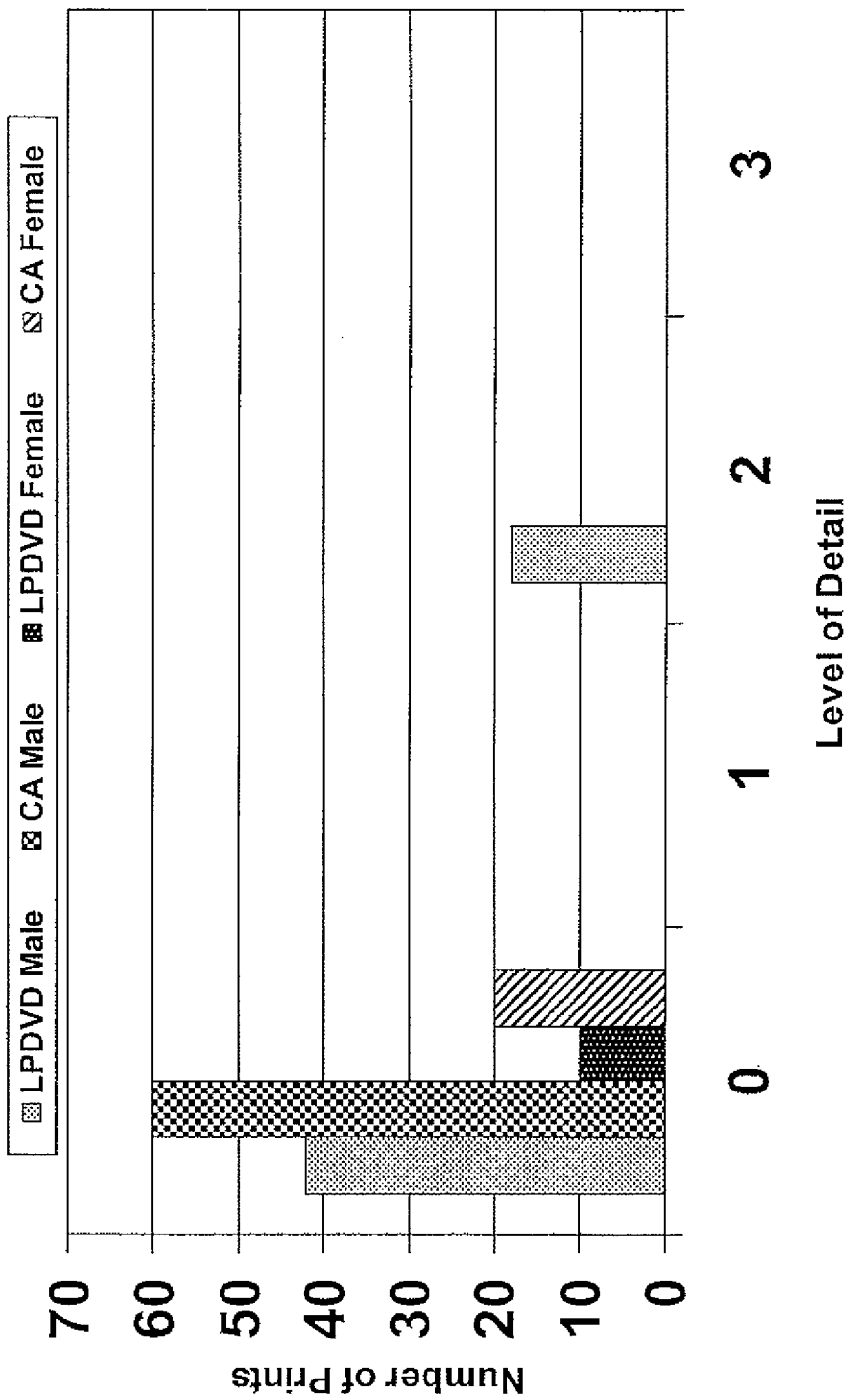
FIG. 4 is a graph showing results of tests performed on the front side of thermal paper substrates 24 hours after fingerprint deposition.
Figure 5:
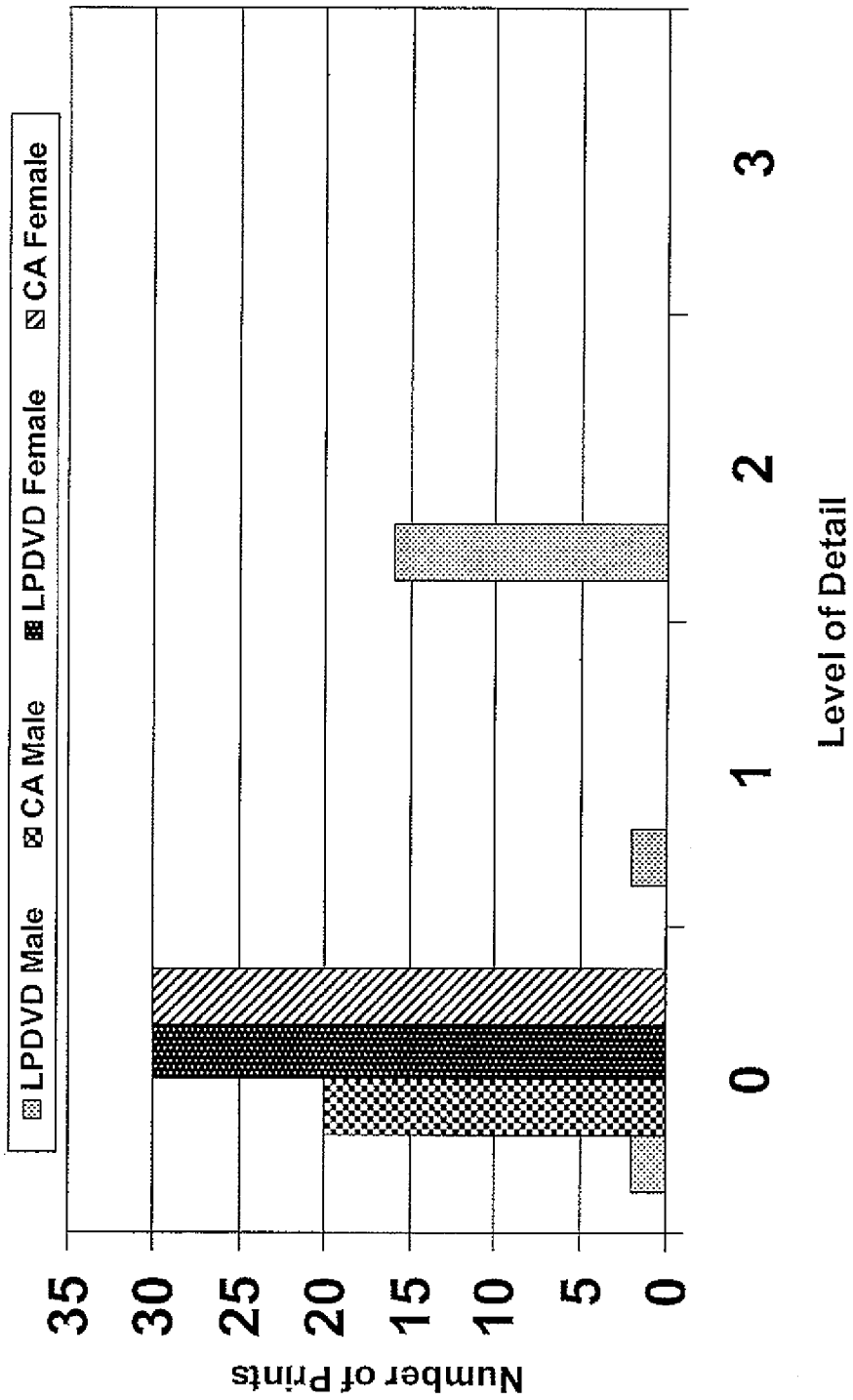
FIG. 5 is a graph showing results of tests performed on the back side of thermal paper substrates 24 hours after fingerprint deposition.

Results obtained from the glass samples (microscope slides) after 24 hours are shown in Table 1 and FIG. 3. The female prints (total n=80) were very poor in quality and did not yield significant results, although 5 Level 2 detail prints were developed using the LPDVD process compared to none for the CA process. The male prints (total n=120) were of much better quality. This can be explained by the lack of oils and fatty acids on the fingers of the volunteers with the female volunteers not producing enough sebum to provide well developed fingerprints on the tested substrates. The LPDVD process yielded successful results with 47 (n=60) male prints showing Level 2 detail. The conventional CA fuming process also yielded favorable results for the male prints, producing 41 (n=60) Level 2 detail prints. Of 51 preferences recorded for male prints the investigating officer preferred those developed by the LPDVD process 30 times.

Figure 8:
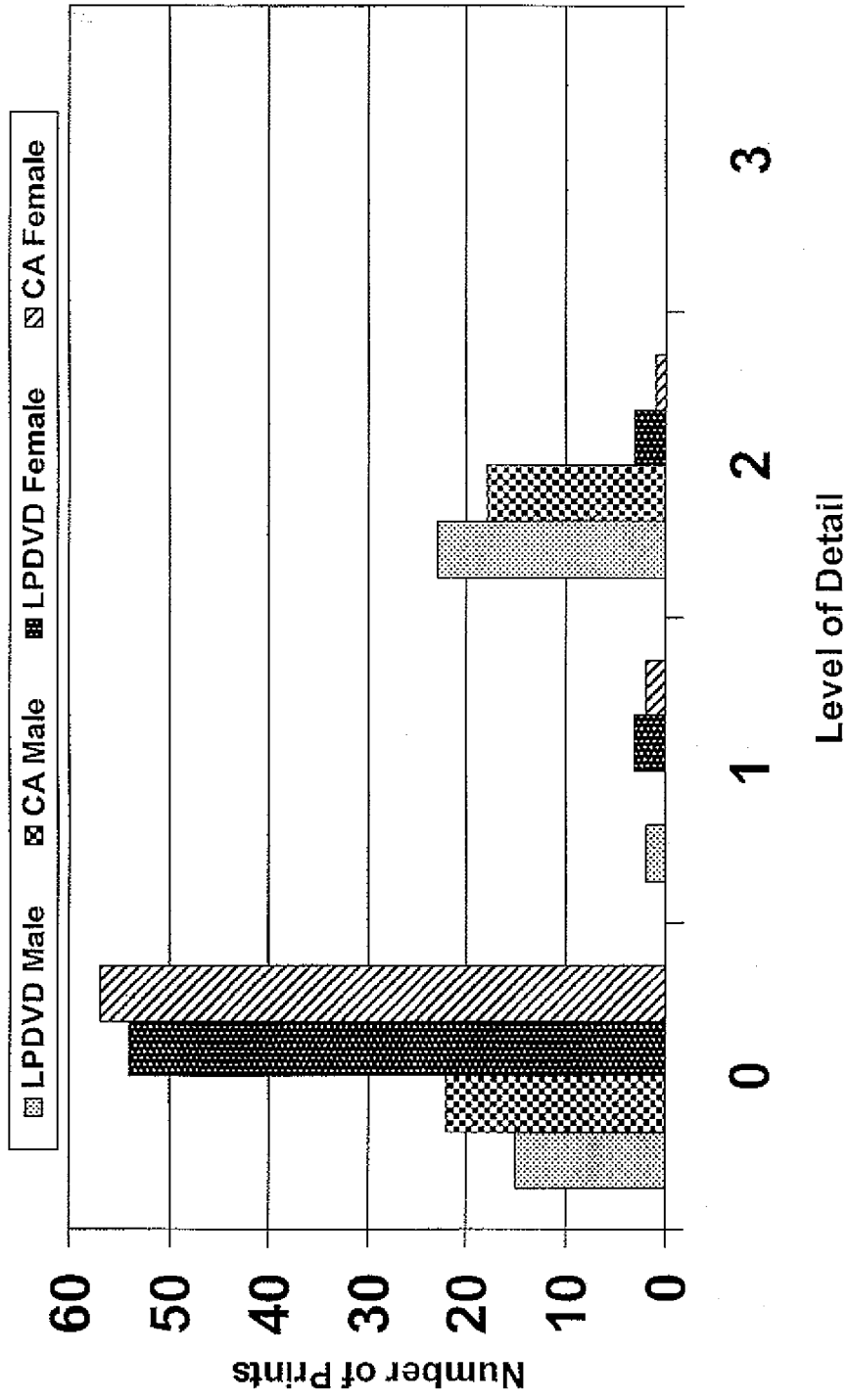
FIG. 8 is a graph showing results of tests performed on glass 60 days after fingerprint deposition.

The results for the 60 day old prints on glass are shown in Table 2 and FIG. 8. Similar results to those for the 24 hour samples were found. The male prints again produced much better results then the female prints, probably because of the low amounts of residues left by the female volunteers. It is also possible that improvements to the sensitivity of the processes could be made. The LPDVD process developed 23 (n=40) of the male prints with Level 2 detail (57.5%) which the CA fuming method developed 18 (n=40) of the male prints with Level 2 detail (45%). Therefore, in this test, the LPDVD process is somewhat better than the conventional CA method.

The tests on thermal paper proved the most intriguing. The results for the 24 hour samples are shown in Table 1 and in FIGS. 4 and 5. The LPDVD process was the only process that was able to develop any latent prints on the front side of thermal paper. In particular, the LPDVD process was able to develop 18 prints (n=60) of male prints with Level 2 detail (30%) whereas the dry ninhydrin process was unable to develop any of the male prints with detail. The LPDVD process was able to develop 10 (n=20) of female prints with Level 2 detail (50%) whereas the dry ninhydrin process was again unable to develop any female prints with detail. A total of 160 prints were processed on the front side of thermal paper with the LPDVD process obtaining 28 prints of Level 2 detail as opposed to the dry ninhydrin method that failed to develop any prints.

The back side of the thermal paper showed similar results with the LPDVD process obtaining 16 prints (n=20) of Level 2 detail (80%) and a total of 18 prints (n=20) of Level 1 and Level 2 detail (90%). The dry ninhydrin method was unable to develop any prints and no female prints were obtained with either process. These results clearly show the superiority of the LPDVD process over the conventional dry ninhydrin process in being able to develop latent prints on thermal paper.

Figure 9:
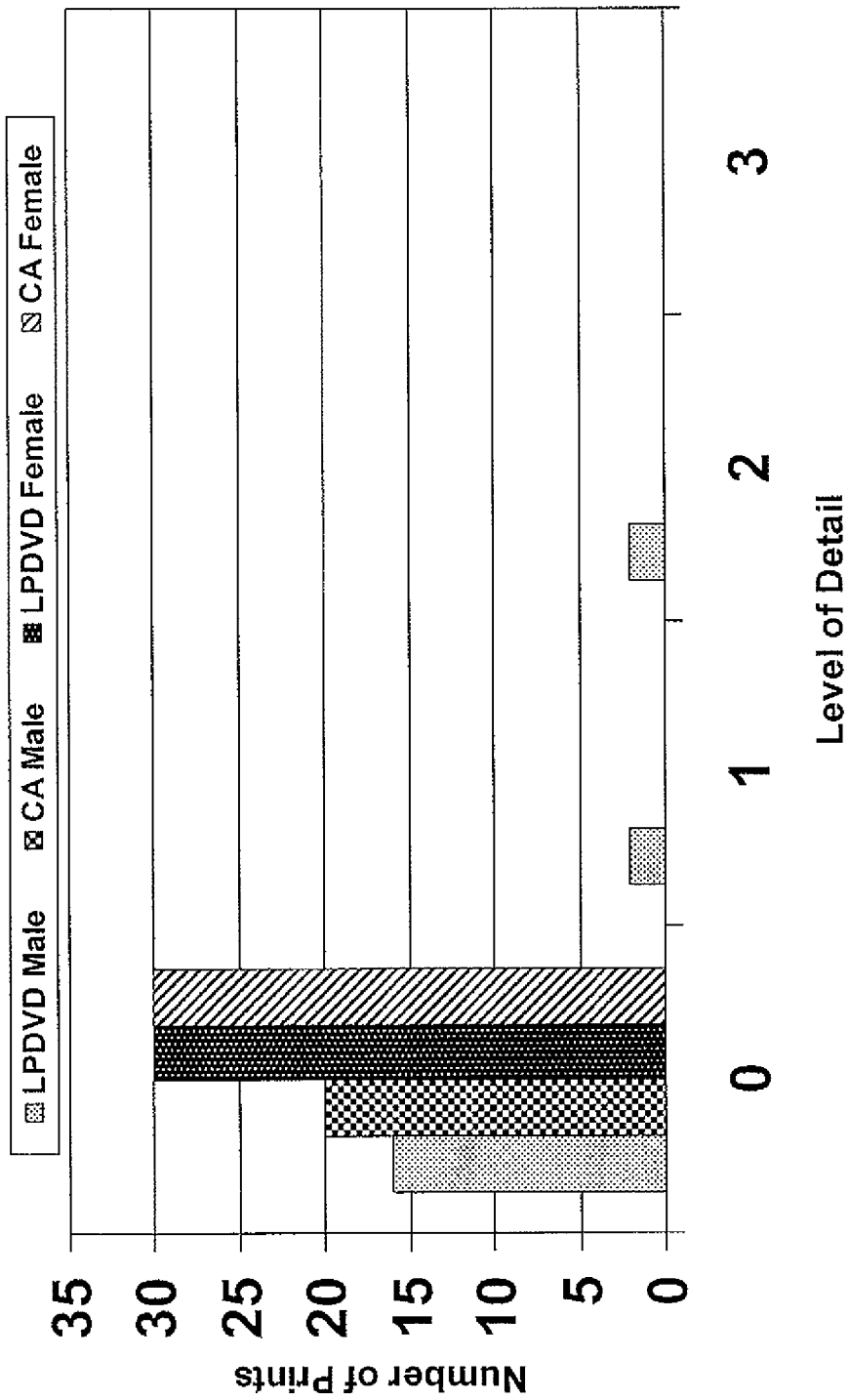
FIG. 9 is a graph showing results of tests performed on thermal paper substrates 60 days after fingerprint deposition.

The results for the 60 day old thermal paper prints are shown in Table 2 and FIG. 9. As noted above, this represents a mixture of front side and back side samples. Only the LPDVD process was able to develop any prints with detail; i.e. 2 prints with Level 1 detail and 2 prints with Level 2 detail. The small number of results did not permit any conclusions to be made.

Overall, the results obtained from the processing of the 24 hour and 60 day old prints proved the viability and usefulness of the LPDVD process according to the present invention. In particular, the 24 hour sample results showed that the LPDVD process is more effective in developing latent prints with identifiable detail on aluminum foil, glass and thermal paper than conventional processes and specifically showed that the LPDVD process was the only process able to develop prints on thermal paper. The CA fuming method was slightly preferred for plastic bag substrates. The 60 day old samples did not produce results that were as dramatic, but still proved that the LPDVD process is comparable to conventional processes. CA fuming was still slightly preferred for both aluminum foil and plastic bags, but LPDVD was more effective for glass. Thermal paper results were not significant as there not enough prints could be developed by any method.

While the above invention is primarily directed to the detection of latent fingerprints on a variety of substrates, other uses have been contemplated For example, the LPDVD process of the present invention may be useful for detecting minute cracks or metal fatigue on metal parts therefore illuminating the need for liquid penetrate inspection (LPI) and providing greater utilization of materials.

It will be understood that the embodiments described herein are merely exemplary, and that one skilled in the art may make variations and modifications without departing from the spirit and scope of the invention. All such variations and modifications are intended to be included within the scope of the invention as described hereinabove. Further, all embodiments disclosed are not necessarily in the alternative, as various embodiments of the invention may be combined to provide the desired result.

What is claimed is:

1. A method for developing latent fingerprints comprising performing the following steps in the order set forth:
   loading source materials into a vapor delivery chamber;
   evacuating the vapor delivery chamber;
   heating the vapor delivery chamber;
   adding a carrier gas to the vapor delivery chamber;
   maintaining heat within the vapor delivery chamber to vaporize the source materials;
   using the carrier gas to transport the vaporized source materials to a vacuum deposition chamber separate from the vapor delivery chamber and holding an article having latent fingerprints to develop; and
   depositing the source material onto the article to develop the latent fingerprints.

2. A method according to claim 1 wherein the source materials are polycyanoacrylate and a dye.

3. A method according to claim 2 wherein the dye is a fluorescent dye.

4. A method according to claim 3 wherein the dye is rhodamine 6G, D2 yellow, ardrox, brilliant yellow, or Photosecure UY1.

5. A method according to claim 2 wherein the dye is a non-fluorescent dye.

6. A method according to claim 5 wherein the dye is an anthraquinone compound.

7. A method according to claim 2 wherein the dye is an infrared dye.

8. A method according to claim 7 wherein the dye is Photosecure N84.

9. A method according to claim 1 wherein the carrier gas is nitrogen.

10. A method according to claim 1 wherein the article is non-porous or porous.

11. A method according to claim 1 wherein the article is metal, glass, plastic or thermal paper.

* * * * *